United States Patent
Hamilton

(10) Patent No.: US 9,505,674 B2
(45) Date of Patent: Nov. 29, 2016

(54) PROCESSES FOR TREATING OLEFIN FEEDSTREAMS AND RELATED OLIGOMERIZATION PROCESSES

(71) Applicant: ExxonMobil Chemical Patents Inc., Baytown, TX (US)

(72) Inventor: Paul Hamilton, Eastleigh (GB)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 14/647,728

(22) PCT Filed: Nov. 8, 2013

(86) PCT No.: PCT/EP2013/073400
§ 371 (c)(1),
(2) Date: May 27, 2015

(87) PCT Pub. No.: WO2014/082838
PCT Pub. Date: Jun. 5, 2014

(65) Prior Publication Data
US 2015/0307414 A1  Oct. 29, 2015

Related U.S. Application Data

(60) Provisional application No. 61/731,367, filed on Nov. 29, 2012.

(30) Foreign Application Priority Data

Jan. 8, 2013 (EP) .................................. 13150474

(51) Int. Cl.
| | | |
|---|---|---|
| C07C 2/02 | (2006.01) | |
| C08F 210/00 | (2006.01) | |
| C07C 2/08 | (2006.01) | |
| C10G 3/00 | (2006.01) | |
| C07C 7/10 | (2006.01) | |

(52) U.S. Cl.
CPC . C07C 2/08 (2013.01); C07C 7/10 (2013.01); C10G 3/00 (2013.01); Y02P 30/20 (2015.11)

(58) Field of Classification Search
CPC ............. C10G 3/00; C07C 2/08; C07C 7/08; C07C 11/02; C07C 11/06; C07C 7/10; Y02P 30/20
USPC .......................................... 585/518; 526/348
See application file for complete search history.

(56) References Cited

U.S. PATENT DOCUMENTS

| | | | |
|---|---|---|---|
| 2,417,892 A * | 3/1947 | Teter ..................... | C07C 209/60 203/DIG. 3 |
| 4,153,638 A | 5/1979 | Bercik et al. | |
| 4,973,790 A | 11/1990 | Beech, Jr. et al. | |
| 5,414,183 A | 5/1995 | Abrevaya et al. | |
| 5,569,790 A | 10/1996 | Frey et al. | |
| 5,672,800 A * | 9/1997 | Mathys ..................... | B01J 29/06 585/520 |
| 5,675,043 A | 10/1997 | Eppig et al. | |
| 6,160,193 A | 12/2000 | Gore | |
| 7,205,448 B2 | 4/2007 | Gajda et al. | |
| 7,238,844 B2 | 7/2007 | Mathys et al. | |
| 7,569,741 B2 | 8/2009 | Butler et al. | |
| 7,744,828 B2 | 6/2010 | Schmidt et al. | |
| 7,786,338 B2 | 8/2010 | Cheng et al. | |
| 7,989,668 B2 | 8/2011 | Godsmark et al. | |
| 2002/0103406 A1 | 8/2002 | Mathys et al. | |
| 2004/0097773 A1 | 5/2004 | Beckmann et al. | |
| 2005/0137442 A1 | 6/2005 | Gajda et al. | |
| 2005/0152819 A1 | 7/2005 | Schmidt et al. | |
| 2007/0213575 A1 | 9/2007 | Godsmark et al. | |
| 2008/0312484 A1 | 12/2008 | Godsmark et al. | |

FOREIGN PATENT DOCUMENTS

| | | |
|---|---|---|
| EP | 1 002 852 | 5/2000 |
| EP | 1 694 617 | 8/2006 |
| GB | 1 131 989 | 10/1968 |
| WO | WO 00/71494 | 11/2000 |
| WO | WO 2007/104385 | 9/2007 |
| WO | WO 2012/078218 | 6/2012 |

OTHER PUBLICATIONS

Egloff et al., Polymerisation with Solid Phosphoric Acid Catalyst, Proceedings of Third World Petroleum Congress, Section IV, pp. 202-214, (1951).
McMahon et al., Polymerization of Olefin as a Refinery Process, Advances in Petroleum Chemistry and Refining, vol. 7, Chapter 5, pp. 285-321, (1963) ("Efficient washing of feed with slightly acidified water is required to maintain this degree of Purity").
UOP sPA catalyst operating guideline manual (1982).
Solid Phosphoric Acid Catalyst C-84 Series and CA-131 Technical Service and Catalyst Manual, Sud Chemie Group, 1996.
Nagai et al., Isolation of Nitrogen-containing Heterocyclic Compounds Contained in Coal Tar Absorption Oil Fraction with Solvent Extraction, Sekiyu Gakkaishi (Journal of the Japan Petroleum Institute), 43 (5), pp. 339-345, (2000).

* cited by examiner

Primary Examiner — William Cheung
(74) Attorney, Agent, or Firm — Darryl M. Tyus

(57) ABSTRACT

Embodiments disclosed herein relate to a process for the oligomerization of olefins, the process including at least one olefin feedstream that includes ammonia and contacting the at least one olefin feedstream with a liquid including alkaline water to remove at least a portion of the ammonia to produce at least one treated olefin feedstream and subsequently contacting the at least one treated olefin feedstream with a catalyst under oligomerization conditions to produce an oligomer product. In several embodiments disclosed herein, the at least one olefin feedstream includes one or more $C_3$-$C_{15}$ olefins, preferably, $C_3$-$C_5$ olefins, any isomer thereof, one or more paraffins having the same or different carbon number as the olefins, and mixtures thereof.

12 Claims, No Drawings

PROCESSES FOR TREATING OLEFIN FEEDSTREAMS AND RELATED OLIGOMERIZATION PROCESSES

CROSS REFERENCE TO RELATED APPLICATIONS

This application is a National Stage Application of International Application No. PCT/EP2013/073400, filed Nov. 8, 2013, which claims foreign priority based on European Patent application EP 13 150 474.8 filed on Jan. 8, 2013, and claims the benefit of Ser. No. 61/731,367, filed Nov. 29, 2012, the disclosures of which are fully incorporated herein by reference in their entireties.

FIELD OF THE INVENTION

Embodiments disclosed herein relate to processes for treating olefin feedstreams. In particular, embodiments disclosed herein relate to processes for treating olefin feedstreams that remove among other things nitrogen containing compounds including, for example, ammonia. The treated olefin feedstreams may then be used in petrochemical processes, such as, for example, oligomerization processes.

BACKGROUND OF THE INVENTION

The condensation reaction of an olefin or a mixture of olefins to form higher molecular weight products is widely known and practiced. This type of condensation reaction is referred to herein as an oligomerization reaction or process, and the products are low molecular weight oligomers which are formed by the condensation of up to 12, typically 2, 3 or 4, but up to 5, 6, 7, or even 8 olefin molecules with each other. "Oligomerization" refers to a process for the formation of oligomers and/or polymers. Low molecular weight olefins (such as, for example, ethylene, propene, 2-methylpropene, 1-butene and 2-butenes, pentenes and hexenes) may be converted by oligomerization over, for example, a solid phosphoric acid catalyst (commonly referred to as "sPa" catalyst) or a molecular sieve catalyst (e.g., a zeolite catalyst), to an oligomer product.

Oligomer products are valuable components of high-octane gasoline blending stock that may be used or blended into a distillate type liquid fuel or as a lubricant, or as a starting material for the production of chemical intermediates and end-products. Such chemical intermediates and end-products include high purity hydrocarbon fluids or solvents, alcohols, detergents/surfactants, and esters such as plasticizer esters and synthetic lubricants.

A number of catalysts may be used in such oligomerization processes. For example, industrial oligomerization reactions employing molecular sieve catalysts are generally performed in a plurality of tubular or chamber reactors, similar to those processes employing sPa catalysts. With sPa catalysts, the pressure drop over the catalyst bed(s) increases gradually over the duration of the run, due to coking and/or swelling of the catalyst pellets and the reactor run is typically terminated when a maximum allowable pressure drop over the reactor is reached. Molecular sieve catalysts do not show pressure drop increases similar to sPa catalysts. Oligomerization reactors using molecular sieve catalysts are therefore characterized by longer reactor run lengths and are typically decommissioned when the catalyst activity has dropped to an unacceptably low level. With these catalysts, the reactor run length that can be achieved is therefore much more sensitive to compounds, impurities, or contaminants in the feedstreams that deactivate the catalyst, such as catalyst poisons.

The art is replete with endeavors that attempt to remove or minimize levels of contaminants or impurities that adversely affect catalyst life and activity. For example, strong bases, such as the proton bases or Bronsted bases, are known poisons for many of the oligomerization catalysts that are acidic, for example, molecular sieve catalysts. Such bases in hydrocarbon streams are often nitrogen containing compounds, such as amines and amides, and they are typically removed from feedstreams for oligomerization reactions and other hydroprocessing reactions. Such organic nitrogen-containing Bronsted bases are characterized by at least one hydrogen atom bound to the nitrogen atom and are known proton acceptors. Other organic nitrogen components do not have any hydrogen atoms bound to the nitrogen and the nitrogen atom may have three bonds to 1, 2 or 3 surrounding carbon atoms. These nitrogen atoms however still have a free electron pair and therefore can still act as a base, termed a Lewis base. Lewis bases are known to be weaker bases as compared to Bronsted bases and therefore are sometimes considered less problematic to acid catalyzed processes.

Numerous attempts have been made to treat feedstreams or feedstocks prior to undergoing hydroprocessing or petrochemical reactions. See, for example, U.S. Pat. No. 4,973,790 (disclosing a process for oligomerization of $C_2$ to $C_{10}$ olefins over a zeolite catalyst comprising a feed pre-treatment step to remove basic nitrogen compounds, for example, amines such as di-ethanol-amine); U.S. Pat. No. 5,675,043 (disclosing processes for treating a hydrocarbon blend containing nitrogen-containing compounds with a solvent having a Hansen polar solubility parameter to effect removal of a portion of said nitrogen-containing compounds therefrom); U.S. Patent Application Publication No. 2002/103406 (disclosing a process for oligomerizing an olefin originating from an oxygenate to olefin process using a nickel based catalyst, the olefin stream having a low nitrogen content, as low as 0.3 ppm by weight); U.S. Patent Application Publication No. 2004/0097773 (disclosing a process for oligomerizing isobutene wherein feedstocks have been treated to remove nitrogen components, for example, acetonitrile and N-methyl-pyrrolidone); U.S. Pat. Nos. 7,205,448, 7,744,828, and U.S. Patent Application Publication No. 2007/0213575 (disclosing the removal of nitrogen compounds, including a number of Lewis base compounds such as nitriles, for example, acetonitrile, N-methyl-pyrrolidone, morpholines such as N-formyl morpholine, pyridine and/or quinoline, from feedstreams); Nagai et al., *Isolation of Nitrogen-containing Heterocyclic Compounds Contained in Coal Tar Absorption Oil Fraction with Solvent Extraction*, Sekiyu Gakkaishi (Journal of the Japan Petroleum Institute), 43 (5), 339-345 (2000) (disclosing using aqueous solutions of methanol or tetrahydrothiophene-1,1-dioxide (sulfolane) to remove heterocyclic compounds containing nitrogen atoms from coal tar oil absorption oil fractions); and SU 1086006 (disclosing using a metal chloride such as $NiCl_2$ in an organic solvent such as propylene carbonate or dimethylsulfoxide or dimethylformamide to remove nitrogen compounds from petroleum products by complexing the metal chloride with the nitrogen compounds). Other background references include U.S. Patent Application Publication Nos. 2005/0137442, 2005/0152819, 2008/0312484, U.S. Pat. Nos. 4,153,638, 5,569,790, 6,160,193, EP 1 002 852 B, GB 1,131,989, WO 2000/71494, and WO 2012/078218.

As can be seen, much effort has been made directed to removing impurities and contaminants from feedstreams where much of the work has been focused on removing alcohols, ketones, organo sulfur compounds, such as, for example, sulfides and thiols or mercaptans, nitrogen containing compounds, such as, for example, nitriles, pyrroles, amines, amides, imides, indoles, cyanates, pyridines, pyrrolidones, and combinations thereof. Although these contaminants and impurities remain important to the efficiency of the oligomerization reaction, little work has been focused regarding ammonia, either alone or with other compounds, and its ability to reduce the efficiency and life and the oligomerization catalyst.

In particular, $C_3$ olefin containing feedstreams create unique challenges with respect to ammonia as compared to other feedstreams such as $C_4$ olefin containing feedstreams. For example, pure propylene has a boiling point of −47.6° C., pure propane has a boiling point of −42° C., and pure ammonia has a boiling point of −33.3° C. Any Ammonia present in a stream containing $C_3$ and $C_4$ molecules (such as isobutane, butane, isobutene, and butenes that have a range of boiling points between −11.7° C. and +3.7° C.), that is fractionated to a $C_3$ rich stream and a $C_4$ rich stream will fractionate with the $C_3$ rich stream. If there is any acetonitrile present (boiling point 81° C.), in the $C_3/C_4$ stream, once fractionated, the acetonitrile will fractionate with the $C_4$ rich stream. Once the separation of the $C_3$ rich stream and $C_4$ rich stream is completed, the challenges associated with ammonia in the $C_3$ rich stream and acetonitrile in the $C_4$ stream are different. This is due to the different type of bases (i.e., Bronsted bases versus Lewis bases) and the different properties of the hydrocarbon stream containing the different nitrogen species. In the fractionation of the $C_3$ rich stream from the $C_4$ rich stream, it is not possible for ammonia to fractionate with the $C_4$ rich stream, or the acetonitrile to fractionate with the $C_3$ rich stream, due to large differences in relative boiling points. Thus, $C_3$ rich feedstreams pose different challenges from past endeavors to remove other nitrogen species from hydrocarbon feedstreams.

One source of such feedstreams include $C_3$ olefin containing Liquefied Petroleum Gas ("LPG") from refinery sources such as Fluidized Catalytic Crackers ("FCC"). Normally, these streams are treated to remove sulphur containing compounds (such as, for example, hydrogen sulphide and mercaptans) These LPG streams may also contain contaminants such as basic nitrogen compounds (including but not limited to ammonia, amines (such as, for example, monoethanolamine), acetonitrile, and propionitrile. As a solution, amine treating and caustic scrubbing are used to remove the many of the sulphur containing compounds.

However, these processes are not effective to remove basic nitrogen compounds such as ammonia. Thus, oligomerization units using acidic catalysts as described above will be vulnerable by the presence of these basic nitrogen compounds. Ammonia is a common nitrogen containing compound in feedstreams and abundantly available, especially in $C_3$ containing feedstreams. Thus, cost effective removal of these nitrogen containing compounds is essential for manufactures of oligomers to ensure economic catalyst performance.

One solution proposed to removing these nitrogen containing compounds such as ammonia is washing olefin feedstreams with water in various contact devices prior to oligomerization. See, for example, U.S. Pat. No. 7,569,741 (suggesting the use of a washing agent including water in a purification process for feedstocks, predominantly aromatic feedstocks, to remove polar impurities). Many oligomerization catalyst suppliers recommend using acidified water. This solution may also be found in the art. See, for example, U.S. Pat. No. 4,973,790 (suggesting the removal of nitrogen containing compounds with water washing, preferably with acidified water) and U.S. Pat. No. 5,414,183 (suggesting the removal of residual products using water washing where the water is usually acidified with a mineral acid to maintain a pH at an optimum level below 7). U.S. Patent Application Publication No. 2007/0213575 and U.S. Pat. No. 7,989,668 disclose treating an olefin-containing hydrocarbon stream comprising an organic nitrogen-containing Lewis base to thereby lower the concentration of the organic nitrogen-containing Lewis base in the olefin-containing hydrocarbon stream and subsequently contacting the treated olefin-containing hydrocarbon stream with a molecular sieve oligomerization catalyst. The reference states that a preferred extraction step is a water wash, because of the ready availability of suitable wash water. It is preferred that the pH of the wash water is not too high, such as at most 9.5, but preferably it is at most 9 and more preferably at most 8. Most preferably the water is slightly acidic, with a pH below 6.5, 6, 5 or even 4. However, the '668 patent only exemplifies a butene stream containing 90% normal butenes that would not present the same challenges with respect to ammonia and $C_3$ containing streams as explained above. As such, the '668 patent's treatment step is directed to the removal nitriles such as acetonitrile.

Egloff et al., *Polymerisation with Solid Phosphoric Acid Catalyst*, Proceedings of Third World Petroleum Congress, Section IV, pages 202-214, (1951) discloses that ammonia and amines, being basic in character, will act to neutralize the acidic catalyst, thereby rendering it inactive. The chemical reaction between these basic substances and the acid in the catalyst causes softening and gradual disintegration. These substances can be eliminated by washing the feed with water in a countercurrent system. It further teaches that where basic nitrogen compounds are known to be present in large quantities, the most effective removal is obtained by the use of water having a pH controlled by sulfuric acid injection. See also, McMahon et al., *Polymerization of Olefin as a Refinery Process*, Advances in Petroleum Chemistry and Refining, Vol. 7, Chapter 5, pages 285-321, (1963) ("Efficient washing of feed with slightly acidified water is required to maintain this degree of purity.")

With respect to washing with acidic water, in order to meet the recommended pH levels on the inlet and outlet of the contacting device, the provision of acid injection and a pH control is required to maintain optimum water pH. Acid injection facilities are costly and present process control challenges as the pH response to changes in acid injection is not linear. Additionally, the presence of acid either corrodes equipment and facilities and makes materials selection to mitigate against potential acid corrosion challenging as well.

Thus, many catalysts and their respective catalyst lives may be profoundly influenced by contaminants, such as, for example, ammonia and other contaminants or impurities found in feedstocks. Therefore, there remains a long-standing need to address the problems associated with contaminants in feedstreams, in particular, ammonia, in $C_3$ olefin containing feedstreams.

SUMMARY OF THE INVENTION

In several classes of embodiment, the invention provides for a process for the oligomerization of olefins, the process comprising providing at least one olefin feedstream that comprises ammonia and contacting the at least one olefin feedstream with a liquid comprising alkaline water to remove at least a portion of the ammonia to produce at least one treated olefin feedstream and subsequently contacting the at least one treated olefin feedstream with a catalyst under oligomerization conditions to produce an oligomer product.

In any of the embodiments describe herein, the at least one olefin feedstream may comprise one or more $C_3$-$C_{15}$ olefins, preferably, $C_3$-$C_5$ olefins, any isomer thereof, one or more paraffins having the same or different carbon number as the olefins, and mixtures thereof.

In any of the embodiments describe herein, the at least one olefin feedstream may comprise propylene and propane and the at least one olefin feedstream may comprise 45 wt % or more combined propylene and propane, alternatively, 60 wt % or more combined propylene and propane, and alternatively, 80 wt % or more combined propylene and propane, based upon the total weight of the feedstream. The alkaline water may have a pH of 8.0 or greater or a pH of from 7.5 to 10.5.

Other embodiments of the invention are disclosed and claimed herein.

DETAILED DESCRIPTION

Before the present compounds, components, compositions, and/or methods are disclosed and described, it is to be understood that unless otherwise indicated this invention is not limited to specific compounds, components, compositions, reactants, reaction conditions, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an," and "the" include plural referents unless otherwise specified.

In several classes of embodiments, the invention provides for processes utilizing solvent extraction to remove nitrogen containing compounds, for example, one or more nitriles, and optionally other components from mixed olefin feedstreams of olefins and paraffins.

Embodiments disclosed herein relate to a process for the oligomerization of olefins, the process including at least one olefin feedstream that includes ammonia and contacting the at least one olefin feedstream with a liquid including alkaline water to remove at least a portion of the ammonia to produce at least one treated olefin feedstream and subsequently contacting the at least one treated olefin feedstream with a catalyst under oligomerization conditions to produce an oligomer product. In several embodiments disclosed herein, the at least one olefin feedstream includes one or more $C_3$-$C_{15}$ olefins, preferably, $C_3$-$C_5$ olefins, any isomer thereof, one or more paraffins having the same or different carbon number as the olefins, and mixtures thereof.

Feedstocks/Feedstreams and Oligomerization Processes

The at least one feedstock or feedstream comprises olefins, paraffins, and other components. As used herein and unless otherwise specified, "feedstock(s)" and "feedstream(s)" may be used interchangeably. In a class of embodiments, the at least one feedstream comprises olefins having from about 2 to about 15 carbon atoms, such as, for example, from about 3 to about 6 carbon atoms and one or more paraffins. As used herein, "olefins" refers to any of the unsaturated hydrocarbons (e.g., compounds consisting essential of hydrogen and carbon atoms) having the formula $C_nH_{2n}$, wherein C is a carbon atom, H is a hydrogen atom, and n is an integer from 1 to 25, typically, from 1 to 15, alternatively, from 3 to 6. As used herein, "paraffins" refers to any of the saturated hydrocarbons having the formula $C_nH_{2n+2}$, wherein C is a carbon atom, H is a hydrogen atom, and n is an integer from 1 to 25, typically, from 1 to 15, alternatively, from 3 to 6. Additionally, in several embodiments, the feedstream may comprise an oligomer, such as, for example, a dimer, for example, one provided by recycling a part of a product stream.

The feedstream may comprise olefins and paraffins having the same or different number of carbon atoms.

In a class of embodiments, the feedstream comprises one or more of propene, butenes, pentenes, hexenes, their isomers, paraffins having the same or different carbon numbers, and mixtures thereof. The process is especially useful for the oligomerization of feedstreams comprising propene, butenes, pentenes, their isomers, other components, and mixtures thereof.

As used herein, "oligomer(s)" or "oligomer product" refers to a polymer molecule (or a mixture of polymer molecules) made from a few monomer units such as, for example, a dimer, a trimer, a tetramer, a mixture thereof, etc. In a class of embodiments, "oligomer(s)" refers to a polymer molecule (or a mixture of polymer molecules) having 20 carbon atoms or less, alternatively, 15 carbon atoms or less, alternatively, 10 carbon atoms or less, alternatively, 9 carbon atoms or less, and alternatively, 8 carbon atoms or less. As used herein, "oligomerization process" refers to any process of catalytically joining monomer units to form the oligomer(s) as defined above. In a class of embodiments, oligomerization process is used synonymously with "polymerization process." As used herein, the term "oligomerization conditions" refers to any and all those variations of equipment, conditions (e.g., temperatures, pressures, etc.), materials, and reactor schemes that are suitable to conduct the oligomerization process to produce the oligomer(s) as known and applied in the art and discussed more below.

The olefins to be oligomerized may be one or more of $C_3$-$C_{15}$ olefins or mixtures thereof including one or more paraffins having the same or different carbon number, alternatively, $C_3$-$C_6$ olefins or mixtures thereof, including one or more paraffins having the same or different carbon number, and alternatively, $C_3$-$C_5$ olefins or mixtures thereof including one or more paraffins having the same or different carbon number.

In a class of embodiments, the feedstream may comprise 45 wt % or more olefins, alternatively, 50 wt % or more olefins, alternatively, 60 wt % or more olefins, alternatively, 70 wt % or more olefins, and alternatively, 80 wt % or more olefins, based upon the total weight of the feedstreams(s).

In another class of embodiments, the at least one feedstream may comprise 45 wt % or more combined olefins and paraffins, alternatively 60 wt % or more combined olefins and paraffins, alternatively 75 wt % or more combined olefins and paraffins, alternatively, 80 wt % or more combined olefins and paraffins, alternatively, 85 wt % or more combined olefins and paraffins, alternatively, 90 wt % or more combined olefins and paraffins, and alternatively, 95 wt % or more combined olefins and paraffins, based upon the total weight of the feedstream(s).

The olefins and paraffins may have the same or different carbon number or may be a mixture of olefins and paraffins have the same and different carbon numbers. For example, in an embodiment of the invention, the at least one feedstream comprises the ranges stated above of propylene and propane but may also have other smaller amounts of other olefins and paraffins having different carbon numbers, such as, for example, butanes and butenes, ethanes and ethylenes, etc.

In another class of embodiments, the at least one feedstream may comprise 60 wt % or more combined $C_3$ olefins and paraffins, alternatively, 70 wt % or more combined $C_3$ olefins and paraffins, alternatively, 80 wt % or more combined $C_3$ olefins and paraffins, alternatively, 85 wt % or more combined $C_3$ olefins and paraffins, alternatively, 90 wt % or more combined $C_3$ olefins and paraffins, and alternatively, 95 wt % or more combined $C_3$ olefins and paraffins, based upon the total weight of the feedstream(s).

In any of the embodiments described herein, the feedstream may be free of aromatic hydrocarbon compounds that consist solely of hydrogen and carbon or be substantially free of aromatic hydrocarbon compounds that consist solely of hydrogen and carbon. As used herein, "substantially free" refers to 25 wt % or less of the aromatic hydrocarbon compound present in the feedstream(s), alternatively, 15 wt % or less, alternatively, 10 wt % or less, alternatively, 5 wt % or less, and alternatively, 1 wt % or less, based upon the total weight of the feedstream(s).

Additionally, the feedstream may comprise isomers of any of the constituents found therein. As used herein, "isomer" refers to compounds having the same molecular formula but different structural formula. Examples may be structural isomers, stereoisomers, enantiomers, geometrical isomers, etc. Typically, the feedstream may comprise at least one isomer of the olefins) or other constituents in the feedstream.

In a class of embodiments, the feedstream may also comprise contaminants or compounds that may hinder catalyst life or productivity. These may include nitrogen, sulfur, chlorine, oxygen containing compounds, and mixtures thereof. Examples of nitrogen containing compounds include nitriles (for example, acetonitrile, propionitrile, etc.), ammonia, amides, amines, pyridines, imides, cyanates, pyrroles, pyrrolidones, and mixtures thereof.

As used herein, "nitrile" is any organic compound that has a nitrile group (or —C≡N functional group). In the nitrile group, the carbon atom and the nitrogen atom are triple bonded together. As used herein, "acetonitrile" is the chemical compound with formula $CH_3CN$. This colorless liquid is the simplest organic nitrile. As used herein, "propanenitrile", "propionitrile", or "ethyl cyanide" is a nitrile with the molecular formula $C_2H_5CN$ and the terms may be used interchangeably. It is also clear liquid. As used herein, "nitrile" may also refer to heavier nitriles. As used herein, "pyrrole" is a heterocyclic aromatic organic compound, a five-membered ring with the formula $C_4H_4NH$. Substituted derivatives may also be referred to as pyrroles.

Examples of sulfur containing compounds include mercaptans such as, for example, methyl mercaptan, ethyl mercaptan, propyl mercaptan, sulfides, such as, for example, dimethyl sulfide, diethyl sulfide, ethyl methyl sulfide, n-propyl sulfide, 1-propane thiol, 2-propane thiol, 1-butane thiol, 1,1-methylethyl thiol, ethylmethyl disulfide, dimethyl disulfide, tetrahydrothiopene, carbonyl sulfide, carbon disulfide and mixtures thereof.

In a class of embodiments, the feedstream may also comprise other compounds that may hinder catalyst life or productivity. These may include linear and cyclic dienes such as butadiene, pentadiene, cyclo pentadiene, and mixtures thereof.

Examples of suitable feedstreams include untreated refinery streams such as Fluidized Catalytic Cracking (FCC), coker, and pygas streams as well as aromatics-containing streams, such as, for example, reformates.

Other examples include Raffinate-1 (RAF-1), Raffinate-2 (RAF-2), and/or Raffinate-3. Typically, Raffinate-1, Raffinate-2, and Raffinate-3 may be regarded as stages in the processing of crude, generally, $C_4$ streams. These streams are usually from olefin steam crackers but may also come from refinery cat-crackers, Butane Dehydrogenation Units, or Gas to Olefin (GTO) Units, or Fisher-Tropsch Units in which case they generally contain the same components but in different proportions with some variation understood by a skilled artisan. The first stage of the process is to remove, by generally solvent extraction or hydrogenation (for example, in a Selective Butadiene Hydrogenation unit) the butadiene which may be as much as 40-45% of the stream. After the butadiene content is substantially reduced in the $C_4$ stream to, for example, 10000 wt ppm or less diene content, alternatively, 5000 wt ppm or less diene content, alternatively, 1000 wt ppm or less diene content, alternatively, 200 wt ppm or less diene content, and alternatively, 10 wt ppm or less diene content, based upon the total weight of the feedstream(s), the remaining product is Raffinate-1. It generally consists of isobutylene, the two normal isomers, butene-1 and butene-2, and smaller quantities of butanes and other compounds. Removal of the isobutylene, usually by reaction with methanol to produce MTBE, the reaction with ethanol to produce ETBE, the production of di-isobutylene (DIB), reaction with water to produce tertiary butyl alcohol (TBA) and the formation of alkyl esters by contact with sulphuric acid produces Raffinate-2. Raffinate 3 (RAF-3) is less common but may also be used. Raffinate 3 may be obtained after separation of 1-butene from Raffinate 2 with a residual 1-butene content of about 1%.

Examples of suitable $C_3$ olefin containing feedstreams include untreated $C_3$ rich refinery streams such as "dilute" or "refinery grade" propylene from a Fluidized Catalytic Cracker (FCC), $C_3$ rich stream from a steam cracker, $C_3$ rich streams from the production of "chemical grade" or "polymer grade" propylene, $C_3$ rich streams from refinery gas recovery units, $C_3$ rich streams from Propane Dehydrogenation Units, $C_3$ rich streams from Gas to Olefin (GTO) Units, or Fisher-Tropsch Units, and $C_3$ rich return streams from polypropylene producing units.

In a class of embodiments, the density at 15° C. (typically as measured by ASTM D4052 unless otherwise noted) of liquid olefin oligimerization feed under pressure varies depending on the composition. For example, a predominately pressurized $C_3$ containing feed may typically have a liquid density at 15° C. of from 0.48 to 0.52 kg/l, a predominately pressurized $C_4$ containing feed may typically have a liquid density at 15° C. of from 0.54 to 0.61 kg/l, a predominately $C_5$ containing feed may typically have a liquid density at 15° C. of from 0.60 to 0.66 kg/l, a mixed pressurized $C_4$ and $C_5$ liquid olefin oligimerization feed may typically have a liquid density at 15° C. of from 0.58 to 0.65 kg/l, and a mixed pressurized $C_3$ and $C_5$ liquid olefin oligimerization feed may typically have a liquid density at 15° C. of from 0.50 to 0.65 kg/l.

By comparison, density of other petroleum type streams are substantially different. Typical petroleum distillate products (e.g., gas oil, diesel, heating oil, etc.) may have a liquid density at 15° C. of 0.82 kg/l or more, fuel oil may have a liquid density at 15° C. typically of 0.90 kg/l or more. Raw crude or shale oil as processed in refineries may have a liquid density at 15° C. typically of 0.79 kg/l or more. Other related products like coal tar may have a liquid density at 15° C. typically of 0.95 kg/l or more.

Thus, in several classes of embodiments disclosed herein, the feedstreams may have liquid densities at 15° C. (in accordance with ASTM D4052) of from 0.45 to 0.70 kg/l, alternatively, from 0.50 to 0.66 kg/l, and alternatively, from 0.54 to 0.65 kg/l. In other embodiments, the feedstreams may have liquid densities at 15° C. (in accordance with ASTM D4052) of 0.94 kg/l or less, alternatively, of 0.89 kg/l or less, and alternatively, of 0.78 kg/l or less.

In another embodiment, the feedstream comprises a mixed C3/C4 FCC light olefin stream that typically comprises ethane, ethylene, propane, propylene, isobutane, n-butane, butenes, pentanes, and other optional components. A specific example of such a feedstream may comprise the following:

|  | Wt % | Mol % |
| --- | --- | --- |
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

In another embodiment, the feedstream comprises a $C_3$ rich FCC stream that typically comprises ethane, ethylene, propane, propylene, isobutane, isobutene, and other optional components. A specific example of such a feedstream may comprise the following:

|  | Wt % | Mol % |
| --- | --- | --- |
| Ethane | 2.8 | 3.9 |
| Ethylene | 0.7 | 1.0 |
| Propane | 17.4 | 16.6 |
| Propylene | 76.7 | 76.7 |
| Isobutane | 1.7 | 1.2 |
| Isobutene | 0.5 | 0.4 |
| Butenes | 0.2 | 0.2 |

In several classes of embodiments the feedstream(s) may comprise a diluent. The diluent may comprise any suitable hydrocarbon such as alkanes or a mixture comprising at least one alkane. The alkanes may be represented the general formula: $C_nH_{2n+2}$, wherein n is a number from 1 to 20, alternatively, from 1 to 10, alternatively, from 1 to 5, and alternatively, from 3 to 4. Examples may include methane, ethane, propane, butane, pentane, and mixtures thereof. In a class of embodiments and when the diluent is present, the feedstream(s) may comprise at least 10%, at least 25%, at least 30%, at least 35%, or at least 40% of the diluent, for example, the alkane such as propane and/or butane, based upon the total volume of the feedstream. Alternatively stated, the diluent may be present in the feedstream in the range from 10% to 40%, alternatively, from 10% to 35%, and alternatively, from 20% to 35% based upon the total volume of the feedstream. The diluent may also be delivered to the reactor(s) through separate feedstreams. When fed separately, the diluent may be fed in amounts to be equivalent to the embodiments wherein the diluent is co-fed with the feedstream. These amounts may not necessarily be the same as the ranges stated above given that more or less of the diluent may be necessary when fed separately to provide an equivalent. In some embodiments, the diluent, when present, may improve reactor continuity.

In another embodiment, the feedstream comprises a $C_3$ rich olefin containing stream that is a mixture of refinery $C_3$ rich streams and diluent stream(s) that typically comprises ethane, ethylene, propane, propylene, isobutane, isobutene, and other optional components. A specific example of such a feedstream may comprise the following:

|  | Wt % | Mol % |
| --- | --- | --- |
| Ethane | 3 | 4.6 |
| Ethylene | 0.1 | 0.2 |
| Propane | 20.3 | 21.3 |
| Propylene | 43.9 | 48.1 |
| Isobutane | 20.2 | 16.1 |
| Isobutene | 0.2 | 0.2 |
| Butenes | 2.4 | 2.0 |
| Butane | 6.5 | 5.3 |
| Pentanes | 3.4 | 2.3 |

Reactors, Reaction Conditions, and Oligomerization Catalyst

The reaction system may include one or more of a fixed bed reactor, a packed bed reactor, a tubular reactor, a fluidized bed reactor, a slurry reactor, a continuous catalyst regeneration reactor, and any combination thereof. They may be operated in any combination such as, for example, in series and/or parallel sequence. In several embodiments, they may be operated in semi-continuous (i.e., continuous but down for routine maintenance), continuous, and/or batch mode.

The oligomerization conditions may include operating temperatures from about 80° C. to about 350° C. Close to and above the upper end of the range, deoligomerization rates increase and may predominate over the oligomerization reaction providing an upper limit to practical operation. More typically, the reaction temperature is from about 130° C. to about 320° C., alternatively, from about 135° C. to about 310° C., and alternatively, from about 160° C. to about 270° C.

The pressure may be in the range of from about 400 psig to about 4000 psig (2860 to 27680 kPa), and alternatively, from about 500 psig to about 1500 psig (3550 to 10440 kPa).

The olefin weight hourly space velocity may be in the range of from about 0.1 hr-1 to about 20 hr-1 or from about 0.5 hr-1 to about 5 hr-1.

In one embodiment, the process is conducted at a temperature of 80-350° C.; an olefin weight hourly space velocity of 0.1-20 hr-1; and a pressure of 2860-27680 kPa.

In another embodiment, the process is conducted at a temperature of 130-320° C.; an olefin weight hourly space velocity of 0.5-15 hr-1; and a pressure of 3550-10440 kPa.

Oligomerization Catalyst and Oligomer Products

One or more catalysts may be used in the oligomerization processes of several embodiments of the invention. Any catalyst may be used so long as it is suitable to oligomerize olefins.

Both homogeneous and heterogeneous catalysts may be used. In a class of embodiments, the oligomerization may be carried out homogeneously, for example, using catalysts soluble in the reaction mixture or heterogeneously, for example, using catalysts insoluble in the reaction mixture.

An example of a homogeneous catalyst includes the IFP (now Axens) DIMERSOL processes which employ a Ni-based homogeneous catalyst. (See, for example, Y. Chauvin et al., Chemistry and Industry, 1974, pages 373-378 and U.S. Pat. No. 3,655,810.) Additionally, U.S. Pat. No. 4,225,743 discloses a homogeneous catalyst system consisting of a nickel (II) salt of octanoic acid, ethylaluminium dichloride, and a free fatty acid.

In contrast, several of the industrial processes use heterogeneous catalysts. Most of these catalysts belong to one of the following groups: a) mineral acids (e.g., sulfuric acid or phosphoric acid) on a support material (e.g., alumina or silica), b) zeolites or other aluminum silicates, "undoped" or "doped" by further metals, in particular, for example, with transition metals, and c) acidic ion exchange resins. Examples may be found in U.S. Patent Application Publication No. 2004/0097773.

In other embodiments, heterogeneous catalysts may be divided into crystalline and amorphous (non-crystalline) catalyst categories. Crystalline catalysts include, without limitation, molecular sieve catalysts such as, for example, zeolite catalysts. Non-crystalline catalysts include, without limitation, solid acid catalysts such as, for example, solid phosphoric acid catalyst (sPa) and supported metal catalysts or supported metal oxide catalysts. Examples include without limitation phosphoric acid-kieselguhr, copper-pyrophosphate-charcoal, and phosphoric acid-coated quartz chips. Commercial processes include the CATPOLY™ Process (UOP and Sud Chemie) employing phosphoric acid on a silica support. Another example of a process that utilizes a solid phosphoric acid oligomerization catalyst is disclosed in U.S. Pat. No. 6,025,533, which describes a process for the production of heavy oligomers by a combination of dehydrogenation and oligomerization. See also the disclosure and examples in European Patent Nos. EP570411B and EP1694617B.

The OCTOL™ Process (UOP/Huels (now Evonik)) employing a nickel containing catalyst on a silica/alumina support is also useful. See *Make plasticizer olefins via n-butene dimerization*, R. H. Friedlander et al., Hydrocarbon Processing, February 1986, pages 31-33, and U.S. Pat. No. 5,177,282. Amorphous silica alumina supports are useful and commonly utilized. Solid acid catalysts may be optionally practiced with promoters such as, for example, $TaF_5$.

In several classes of embodiments of the invention, the catalysts utilized in the oligomerization processes of embodiments of the invention may be any suitable zeolite catalyst(s) capable of oligomerizing olefins. Exemplary methods and materials are provided in WO 2012/033562, U.S. Pat. No. 4,973,790, and U.S. Patent Application No. 2012/0022224. Zeolites are the aluminosilicate members of the family of microporous solids known as "molecular sieves." The term molecular sieve refers to a particular property of these materials, i.e., the ability to selectively sort molecules based primarily on a size exclusion process. This is due to a very regular pore structure of molecular dimensions. The maximum size of the molecular or ionic species that can enter the pores of a zeolite is controlled by the dimensions of the channels. These are conventionally defined by the ring size of the aperture, where, for example, the term "8-ring" refers to a closed loop that is built from 8 tetrahedrally coordinated silicon or aluminum atoms and 8 oxygen atoms. These rings are not always perfectly symmetrical due to a variety of effects, including strain induced by the bonding between units that are needed to produce the overall structure, or coordination of some of the oxygen atoms of the rings to cations within the structure. Therefore, the pores in many zeolites may not be cylindrical.

In an embodiment, the at least one zeolite catalyst may include a medium pore size molecular sieve having a Constraint Index of about 1 to about 12. Constraint Index and a method of its determination are described in, for example, U.S. Pat. No. 4,016,218.

Examples of the at least one zeolite catalyst include those of the TON structure type (for example, ZSM-22, ISI-1, Theta-1, Nu-10, and KZ-2), those of the MTT structure type (for example, ZSM-23 and KZ-1), those of the MFI structure type (for example, ZSM-5, ZSM-5b, etc.), those of the MFS structure type (for example, ZSM-57), those of the MEL-structure type (for example, ZSM-11), those of the MTW structure type (for example, ZSM-12), those of the EUO structure type (for example, EU-1), those of the AEL structure type (for example, SAPO-11), members of the ferrierite family (for example, ZSM-35) and members of the ZSM-48 family of molecular sieves (for example, ZSM-48). Other examples include MWW (e.g., MCM-22, MCM-48), MOR, or beta type catalysts. As used herein, the term "structure type" is used as described in the Structure Type Atlas, Zeolites 17, 1996.

In an embodiment, the at least one zeolite catalyst is selected from at least one of ZSM-5, ZSM-5b, ZSM-11, ZSM-12, ZSM-18, ZSM-22, ZSM-23, ZSM-35, ZSM-38, ZSM-48, ZSM-50, ZSM-57, and mixtures thereof.

In a class of embodiments, the at least one zeolite catalyst comprises molecular sieves having pores formed by 10-membered rings of tetrahedrally coordinated atoms, such as molecular sieves having the TON or MFS structure type.

In an embodiment of the invention, the catalyst composition comprises a crystalline aluminosilicate having an FAU, an EMT or a combination of FAU and EMT framework types as described in, for example, PCT/EP2012/068297, filed Sep. 18, 2012, the catalyst having cobalt and at least one alkaline earth metal selected from calcium, barium, strontium and mixtures thereof within its intracrystalline cages. The crystalline aluminosilicate of the FAU, the EMT, or a combination of the FAU and EMT framework types may have a composition according to formula (I):

$$Co_xM1_yM2_zAl_pSi_{192-p}O_{384} \qquad (I)$$

wherein:
p is the number of aluminium atoms per mol of aluminosilicate, and p is at least 40 but is not greater than 96;
x is the number of Co atoms per mol of aluminosilicate and x is at least 4, but is not greater than (p/2)−5;
M1 is calcium, barium, strontium or a mixture thereof, preferably calcium;
y is the number of M1 atoms per mol of aluminosilicate, and y is at least 5, but is not greater than (p/2)−x;
M2 is sodium, potassium or a mixture thereof, preferably sodium;
z is the number of M2 atoms per mol of aluminosilicate, and z≥0 and z=p−2x−2y.

In an embodiment, the crystalline aluminosilicate is of formula (I), in which p is at least 50, but is not greater than 76, x is at least 4 and is not greater than 10, y is at least 10 and is not greater than 16 and z>0 and z=p−2x−2y.

Mixtures of two or more of catalysts may be used in the processes. For example, the mixture may include ZSM-22 and ZSM-57 or ZSM-22 and ZSM-5 or ZSM-57 and ZSM-5. The at least one zeolite catalyst may also be combined with other catalysts such as a solid phosphoric acid (sPa) catalyst or other acid catalysts.

In several classes of embodiments, the at least one zeolite catalyst is used in its H— or acid form.

The at least one zeolite catalyst may have an average crystallite size of up to 15 μm, such as within the range of from 0.01 to 6 μm, alternatively, from 0.05 to 5 μm, and alternatively, from 0.1 to 3 μm. As used herein, "average crystallite size" refers to the arithmetic average of the diameter distribution of the crystals on a volume basis.

In several embodiments, an as-synthesized molecular sieve is advantageously converted to its acid form, for example, by acid treatment, e.g., by HCl, acetic acid, etc. or by ion exchange, for example, ammonium ion exchange. Subsequently, it may undergo calcination before use. The calcined materials may be post-treated, such as by steaming.

For example, the at least one zeolite catalyst may be produced by any suitable method. One technique includes heating a reaction mixture containing a source of silicon oxide, a source of aluminum oxide and, if appropriate, an organic promoter, for example, a nitrogen or phosphorus-containing organic base, together optionally, with an alkali metal base, and separating the porous aluminosilicate crystals (zeolite precursor crystals) formed. The precursor crystals are then calcined in air or oxygen at a temperature exceeding or about 500° C., for example, at a temperature of 550° C. for about 10 to about 20 hours. As recognized in the art, calcination temperatures and durations may vary depending on the type of zeolite catalyst or combination of zeolite catalysts selected. In one embodiment, the calcined material is exchanged with ammonium ions ($NH_4+$) and subjected to conditions under which the ammonium ions decompose, with the formation of ammonia and a proton, thus, producing an acidic form of the at least one zeolite catalyst. Alternatively, the acidic form of the catalyst may be obtained by acid exchange with hydrochloric acid, acetic acid, etc. If desired, however, the calcined material may be used as a catalyst without first being exchanged with ammonium ions, since the material already possesses acidic sites.

Ammonium exchanged and calcined monodimensional 10-rings zeolites (e.g., ZSM-22 and ZSM-23) may be treated to selectivate their surface, thereby, forming a selectivated catalyst. This selectivation may be achieved in numerous ways. In an embodiment, the at least one zeolite catalyst may be titrated with an organic nitrogen base, such as collidine. See, for example, U.S. Pat. No. 5,026,933. Another example is by depositing a crystalline Si:Al layer on a core of zeolite where this layer has a higher Si:Al ratio than the untreated zeolite. See, for example, U.S. Pat. No. 6,013,851.

Although much of the discussion above is directed to aluminosilicate zeolites, it is possible to use material in which silicon and aluminum have been replaced in whole or in part by other elements, for example, any one or more of a Group 2 to Group 15 atom. For example, silicon may be replaced by or contacted with germanium and aluminum or may be replaced with boron, gallium, chromium, and iron. As used herein, these materials containing such replacement lattice elements may also be termed zeolites.

Exemplary catalyst materials and processes for making and using may also be found in U.S. Pat. Nos. 3,960,978; 4,016,218; 4,021,502; 4,381,255; 4,560,536; 4,919,896; 5,446,222; 5,672,800; 6,143,942; 6,517,807; 6,884,914; U.S. Patent Application Publication No. 2006/0199987; EP 746 538 A; WO 1994/12452; WO 2005/118512; WO 2005/118513; WO 2007/006398; and WO 2008/088452. See also "Atlas of Zeolite Structure Types," Eds. W. H. Meier, D. H. Olson and Ch. Baerlocher, Elsevier, Fourth Edition, 1996.

The at least one zeolite catalyst may be contacted with at least one binder to form a composition that may be extruded into an extrudate as discussed in WO 2012/033562. The at least one binder may be a metal oxide and/or a clay. Suitable exemplary binder materials include at least one of alumina, silica, titanate, an aluminosilicate, clay, and mixtures thereof. In an embodiment, the binder is aluminum oxide ($Al_2O_3$) or commonly referred to as alumina.

For example, in an embodiment, the composition to be extruded into an extrudate may comprise alumina and ZSM-22 or the composition may comprise alumina and ZSM-57. In a class of embodiments, the composition to be extruded into an extrudate may comprise from 10:90 to 90:10, alternatively, from 20:80 to 80:20, of the at least one zeolite catalyst to the at least one binder by weight.

In an alternative class of embodiments, the composition may comprise from 1 to 99 wt % of the at least one zeolite catalyst based upon the total weight of the composition, alternatively, from 20 to 80 wt % of the at least one zeolite catalyst based upon the total weight of the composition, alternatively, from 25 to 75 wt % of the at least one zeolite catalyst based upon the total weight of the composition, alternatively, from 30 to 75 wt % of the at least one zeolite catalyst based upon the total weight of the composition, and alternatively, from 40 to 75 wt % of the at least one zeolite catalyst based upon the total weight of the composition. The remainder of the composition may be or comprise of one or more binders and/or one or more other additives or processing aids.

The composition comprising the product of the at least one zeolite catalyst and the at least one binder may extruded by any process that is capable of producing an extrudate. As used herein, an "extrudate" is the resulting particle of a material that has been extruded through a die. As used herein, a "particle" refers to a discrete unit of material structure as discussed in Hawley's Condensed Chemical Dictionary, Richard J. Lewis Sr., 13th ed., 1997, John Wiley & Sons, Inc., page 840. As used herein, "extrusion" is the process of directing, generally, using some type of mechanical force, a material through a die, for example, a metal die, typically, followed by cutting, cooling, and/or chemical hardening. Extrudates may have many shapes and may be distinguished by their shape. Examples of extrudates include but are not limited to pellets, cylindrical (solid or hollow) extrudates, trilobe extrudates, quadrulobe extrudates, etc. In several classes of embodiments, the extrudates are lobed particles comprising two or more lobes, alternatively, three, four, or more lobes. As used herein, "lobe" refers to any projecting part, for example, at least one rounded projecting part.

A typical, exemplary process for making extrudates proceeds as follows. At least one catalyst and at least one binder are mixed using any suitable method, such as mulling or kneading. The mixing is generally carried out at a temperature in the range of from 1 to 200° C. but generally at ambient temperature.

The composition is then directed to an extruder usually with a force applied, for example, a mechanical force provided by a screw. The material is then pushed through a die or an orifice to create elongated objects of a fixed cross-section. The shape of the extrudate is dependent on the opening of the cross-section. Any conventional extruder may be used.

The composition to be extruded may also include one or more extrusion aids. An extrusion aid helps the mixing, mulling, and extruding operation, and may improve the mechanical and/or physical properties of the extrudate such as crush strength, surface area, pore size, or pore volume. For example, an extrusion aid may promote bridging of inorganic particles during the kneading, molding, drying, and calcination, and/or ensure the mechanical stability of the extrudate during extrusion and calcination. Extrusion aids may also help disperse solvent more homogeneously throughout the composition. Extrusion aids are well known and a listing of some extrusion aids including additional information may be found in, for example, WO 2008/088452.

The extrudate may be dried. The drying process removes at least a portion or all of solvents (e.g., water, alcohols, etc.) from the extrudate. The drying may be performed at atmospheric pressure or under vacuum. The drying may occur in air or an inert atmosphere. The amount of water present in the air may be controlled and/or regulated by the use of air driers (and/or desiccants) and by the use of air moisture measurement.

The extrudates generally have an average particle size of from about $\frac{1}{8}^{th}$ inch to about $\frac{1}{20}^{th}$ inch. In other embodiments, the extrudates generally have an average particle size from about 1.5875 mm ($\frac{1}{16}^{th}$ inch) or less or, alternatively, from 1.2700 mm ($\frac{1}{20}^{th}$ inch) or less. In another embodiment, the extrudates generally have an average particle size of from 1.6 mm (about $\frac{1}{16}^{th}$ inch) or less or, alternatively, from 1.3 mm (about $\frac{1}{20}^{th}$ inch) or less. As used herein, "average particle size" with reference to the extrudate refers to the arithmetic average of the diameter distribution of the extrudate, for example, weight based particle size. In other embodiments, the extrudate may have an average particle size of at least about or from 0.1 mm, 0.2 mm, 0.3 mm, 0.4 mm, or 5 mm up to and including about 1.3 mm, 1.5 mm, 1.6 mm, 2.0 mm, or 2.5 mm, including any range or combination of lower/upper ends disclosed therein. Methods of measuring the extrudates are known and any suitable method may be used. Sieving, microscopy (e.g., electron microscopy), laser techniques have all been proposed and are useful. A preferred example includes sieving using a mesh size in accordance with ASTM 16 and proceeding with the method of measurement provided in British Standard (BS) 1796-1: 1989 cross-referenced as ISO 2591-1: 1988. This procedure is applied and used in the claims unless otherwise stated given its ease and convenience on a commercial scale to quickly isolate a large volume of particles having particular average particle size(s). For more background information, see Table 2.1 of *Powder Sample and Particle Size Determination* by Terence Allen, 2003, Elsevier Science and Technology Books, ISBN 9780444515643.

In a class of embodiments, for a given population of extrudates, not all members need to be uniform and the given population may comprise non-uniform members taking into account irregularities and/or differences that may result in the manufacturing process, handling/transport, defects that develop during use or regeneration, contaminants, use of one more different types of extrudates (for example, using extrudates having different lobe numbers (including but not limited to cylinder, trilobe, quadrulobe, etc.) or using extrudates having different particle sizes, post-manufacture crushing, etc. As used herein, "uniform" refers to having the same form and size. In general classes of embodiments, a given class of extrudates comprises 30% or more uniform members, alternatively, 40% or more uniform members, alternatively, 50% or more uniform members, alternatively, 60% or more uniform members, alternatively, 70% or more uniform members alternatively, 80% or more uniform members, and, alternatively, 90% or more uniform members, based upon the total given population.

For more information regarding the extrusion process and extrudates and their use, see WO 2007/006398; WO 2008/088452; U.S. Patent Application Publication Nos. 2006/0199987; 2009/0216056; and EP 0 220 933 A.

In another class of embodiments, the composition comprising the contact product of the at least one zeolite catalyst and the at least one binder may formed into a spheroid particle by any process that is capable of producing a spheroid structure from the composition. As used herein, "spheroid particle" may refer to any ellipsoid structure. As used herein, "ellipsoid" may be described as an ellipse that has been rotated about at least one of its axis. In a class of embodiments, the spheroid particle may have two equal semi-diameters. The spheroid particle may be one or more of a prolated spheroid (elongated), oblate spheroid (flattened), and sphere itself. As used herein, "spheroid particle" may also refer to two or three dimensional ovoid particles, for example, an ovum (egg). As used herein, "particle(s)" refers to discrete units of material structure as discussed in Hawley's Condensed Chemical Dictionary, Richard J. Lewis Sr., 13th ed., 1997, John Wiley & Sons, Inc., page 840. For the sake of brevity, when spheroid particle is used it may refer to any definition as defined herein as well as refer to one or more of the spheroid particles defined herein. Exemplarily methods and materials may be found in, for example, U.S. Application Publication No. 2012/0022224.

In a class of embodiments, the spheroid particle may be produced by the spherical granulation of a composition by a vibrational dropping process. This technology is commercially available from Brace GmbH, Alzenau, Germany. In general, the technology introduces a liquefied composition through a vibrating nozzle system wherein the exiting stream breaks up into uniform droplets. When dropped or released from the system, the surface tension of the droplets shapes them into a spheroid. Following, the droplets undergo a solidification step. Solidification may be achieved in a gaseous medium through cooling, drying, and/or in liquid medium. The resulting materials are spheroid particles.

In another class of embodiments, the spheroid particle may be produced by a spheronization process. One such process or technology is known as the MARUMERIZER™ process (developed by Fuji Paudal of Osaka, Japan) and is available from LCI Corp., Charlotte, N.C. In general, the process involves the formation of marumes or spheronizing noodles of a given composition. The composition is then fed into a MARUMIZER apparatus which operates by centrifugal force on the noodles to form them into spheronized particles or spheroid particles.

See also WO 97/22680, WO 02/24755, EP 0 046 535 A, EP 2 095 866 A, GB 1 418 445 A, U.S. Pat. Nos. 3,277,520, 3,584,334, 3,741,703, 3,743,464, 5,464,593, 6,923,984, and U.S. Patent Application Publication No. 2005/0054516 for more information and details as to how to produce spheroid particles.

As used herein, "average particle size" with reference to the spheroid particle refers to the arithmetic average of the diameter distribution of the spheroid particles. The spheroid particle may have an average particle size of at least about or from 0.1 mm, 0.2 mm, 0.3 mm, 0.4 mm, or 0.5 mm up to and including 1.0 mm, 1.5 mm, 2.0 mm, 2.5 mm, 3.0 mm, 4.0 mm, or 5.0 mm, including any range disclosed therein. Methods of measuring the spheroid particle are known and any suitable method may be used. Examples include electron microscopy or sieving using a mesh size in accordance with ASTM 16. Methods of measurement and definitions of particle diameters are presented in Table 2.1 of Powder Sample and Particle Size Determination by Terence Allen, 2003, Elsevier Science and Technology Books, ISBN 9780444515643, and are applied herein. In a class of embodiments, a sieving method is applied including using one or more mesh screens to concentrate particles having particular average particle sizes. A preferred method of measurement is provided in British Standard (BS) 1796-1: 1989 cross-referenced as ISO 2591-1: 1988. This method is applied unless otherwise stated given its ease and convenience on a commercial scale to quickly concentrate a large volume of particles having a particular average particle size.

In a class of embodiments, for a given population of spheroid particles, not all members need to be uniform and the given population may comprise non-uniform members in shape taking into account irregularities that may result in the manufacturing process, handling/transport, defects that develop during use or regeneration, contaminants, etc. As used herein, "uniform" refers to having the same form. In general classes of embodiments, a given class of spheroid particles comprises 30% or more uniform members, alternatively, 40% or more uniform members, alternatively, 50% or more uniform members, alternatively, 60% or more uniform members, alternatively, 70% or more uniform me alternatively, 80% or more uniform members, and, alternatively, 90% or more uniform members, based upon the total given population.

Feedstream Treatment

Washing

In a large class of embodiments of the invention, the at least one olefin feedstream is contacted with a liquid comprising alkaline water. As used herein unless otherwise stated, "alkaline" or "alkaline water" shall refer to any water-containing liquid having a pH of 7.0 or greater, alternatively, 7.5 or greater, alternatively, 8.0 or greater, alternatively 8.5 or greater, alternatively, 9.0 or greater, alternatively, 9.1 or greater, and alternatively, 9.5 or greater. In other embodiments, the liquid or alkaline water has a pH from 7.5 to 10.5, alternatively, from 8.0 to 10.5, alternatively, from 9.0 to 10.5, and alternatively, from 9.1 to 10.5.

In several embodiments of the invention, the liquid may contact the at least one feedstream in an amount of from about 1 wt % to about 100 wt %, alternatively, from about 1 wt % to about 30 wt %, alternatively, from about 5 wt % to about 25 wt %, and alternatively, from about 5 wt % to about 20 wt %, based upon the total weight of the feedstream.

The water may be supplied from any suitable source. For example, the water may include deionized water, treated water, potable water, boiler feed water, steam condensate, demineralized water, and combinations thereof, for example.

The contact may occur in any manner known to one skilled in the art. For example, the contact may occur in a single stage (e.g., a tank or drum) or in an extraction unit (e.g., multiple stages). One or more wash towers or columns may also be useful. In particular embodiments of the invention, washing occurs with the liquid comprising the water with a countercurrent flow to the feed in a column containing flow-distribution media such as trays or packing.

In a class of embodiments, a simple, multistage washing is applied and may be run continuously or semi-continuously as needed. In one embodiment of the invention, washing comprises an extraction step or a plurality of extraction steps, which may be in parallel and/or series. In an embodiment, a preferred embodiment comprises the use of a multistage countercurrent extraction column. Such a column may comprise from 2 to 10 stages, alternatively, from 2 to 8 stages, and alternatively, from 4 to 8 stages, or preferably 6, 7, 8, or more stages.

As the stage efficiency may be only 50%, or depending on hydraulics even only 15%, the number of actual stages may be from 8 to 50, alternatively, from 10 to 35, alternatively, from 12 to 25, and alternatively, from 14 to 18.

In a specific embodiment of the invention, the at least one olefin feedstream may be contacted with a liquid comprising alkaline water, the contacting may comprise an extraction step including a plurality of extraction steps. The extraction may be performed in a multistage countercurrent extraction column, optionally, having from 4 to 8 stages.

In any of the embodiments described herein, the at least one olefin feedstream may be contacted with a liquid comprising alkaline water, the contacting may comprise a water wash operating with a ratio of wash water flow to hydrocarbon flow of 0.1 to 1.5 on a liquid volume basis. The washing may occur at any suitable temperature. Examples include from 1° C. to 100° C., alternatively, from 5° C. to 75° C., and alternatively, from 5° C. to 50° C.

In a class of embodiments, the ammonia content or nitrogen present from ammonia in the feedstream(s) before washing may be about 5 wt ppm or more, alternatively, 10 wt ppm or more, alternatively, 20 wt ppm or more, alternatively, 25 wt ppm or more, alternatively, 30 wt ppm or more, alternatively, 32 wt ppm or more, and alternatively, 35 wt ppm or more, calculated on an atomic basis by weight (wt ppm) unless otherwise indicated.

In a class of embodiments, the ammonia content or nitrogen present from ammonia in the feedstream(s) after washing may be about 1.0 wt ppm or less, alternatively, 0.8 wt ppm or less, alternatively, 0.5 wt ppm or less, alternatively, 0.3 wt ppm or less, 0.2 wt ppm or less, and alternatively, 0.1 wt ppm or less calculated on an atomic basis by weight (wt ppm) unless otherwise indicated.

In any of the embodiments described above, the washing, comprising one or more washing steps, may remove 95% or greater of ammonia from the at least one feedstream, alternatively, 98% or greater of ammonia from the at least one feedstream, and alternatively, 99% or greater of ammonia from the at least one feedstream.

In a class of embodiments, washing within the pH ranges described above and with a water to hydrocarbon mass ratio of from 0.05 to 0.75, alternatively, from 0.10 to 0.25, alternatively, from 0.10 to 0.20, or about 0.15 or about 0.13, a 30:1 or greater reduction of ammonia to the feedstream may be achieved to produce a treated feedstream, and in several embodiments as much as 40:1 or greater reduction of ammonia to the feedstream may be achieved, and alternatively, as much as 50:1 or greater reduction of ammonia to the feedstream may be achieved. Alternative ranges also include a 20:1 or greater reduction of ammonia to the feedstream, and a 10:1 reduction of ammonia to the feedstream, to produce a treated feedstream. The reduction of ammonia in the feedstream may occur with or without control of the pH in the alkaline water.

In any of the embodiments described herein, the washing process may occur in the absence of a hydrolysis converter (as described in U.S. Pat. No. 5,414,183, col. 4, lines 35-60) prior to the washing.

Solvent Extraction

The at least one feedstream may also undergo a solvent extraction step prior to oligomerization. Examples of preferred solvent extraction methods may be found in WO 2012/078218. Solvent extraction also referred to as liquid-liquid extraction and partitioning is a method to separate compounds based on their relative solubilities, for example, in at least two immiscible liquids or phases. It generally proceeds as an extraction of a substance from one liquid phase into another liquid phase wherein each liquid phase may comprise the same or different solvent(s). In particular, it generally attempts to separate a substance from a mixture by dissolving that substance in a suitable solvent and removing the substance and solvent from the mixture. The mixture may then proceed to further processing to produce desired end-products.

In several classes of embodiments, the extraction process or contacting at least one feedstream with at least one solvent may be performed in the temperature range of from −40° C. to 100° C., alternatively, from −25° C. to 75° C., alternatively, from −30° C. to 75° C., alternatively, from −25° C. to 60° C., and alternatively, from −15° C. to 50° C. In a class of embodiments, extraction processes may occur at ambient or sub ambient temperatures. In several embodiments, the pressure should be at least high enough to keep both phases in essentially the liquid state to facilitate separation of the two phases.

The extraction process may be executed in the co-current mode, in which the immiscible liquids (i.e., at least one feedstream and at least one solvent) flow in the same direction. Alternatively, the extraction process may be executed in the counter-current mode, where the immiscible liquids (i.e., at least one feedstream and at least one solvent) flow in opposite directions.

The solvent extraction processes employ at least one solvent. As used herein, "sulfone" or "sulfone compounds" refers to a group of organosulfur compounds containing a sulfonyl functional group. The sulfonyl group is a sulfur atom doubly bonded to two oxygen atoms. The sulfur-oxygen double bond is highly polar, allowing for its high solubility in water, while the four carbon ring provides non-polar stability. In a class of embodiments, the at least one solvent comprises sulfolane (also known as tetramethylene sulfone and 2,3,4,5-tetrahydrothiophene-1,1-dioxide).

In another class of embodiments, the at least one solvent comprises one or more of an alkyl/alkenyl/aryl carbonate. As used herein, "alkyl" refers to a hydrocarbon group which may be derived from an alkane by dropping one or more hydrogens from the alkane, such as, for example, a methyl group, an ethyl group, a propyl group, etc. As used herein, "alkenyl" refers to an unsaturated hydrocarbon group containing one or more pairs of carbon atoms linked by a double bond. Examples include an ethylene group, a propylene group, etc. As used herein, "aryl" refers to a hydrocarbon group that forms a ring structure characteristic of aromatic compounds such as, for example, benzene, naphthalene, phenanthrene, anthracene, etc., and typically possess alternate double bonding within its structure. An aryl group is thus a group derived from an aromatic compound by dropping one or more hydrogens from the aromatic compound such as, for example, phenyl group, etc. As used herein, "hydrocarbon" or "hydrocarbon group" refers to compounds or a group of molecules consisting essentially of hydrogen and carbon. The hydrocarbon or hydrocarbon group may be cyclic, linear, branched, substituted, etc. The at least one solvent may comprise one or more, independently the same or different, of the alkyl/alkenyl/aryl carbonates as described above and, optionally, other solvents. In a class of embodiments, the at least one solvent comprises propylene carbonate.

In other embodiments, the at least one solvent may comprise glycols and/or water. Suitable glycols may include any organic alcohol compound that comprises at least two hydroxyl groups (OH) attached to different carbon atoms. Exemplary molecules may include ethylene glycol (1,2-ethanediol), tri-ethylene glycol (2-[2-(2-hydroxyethoxy)ethoxy]ethanol), propylene glycol (1,2-propanediol), 1,3-butanediol, 1,4-butanediol, 2-ethyl-1,3-hexanediol, 2-methyl-2-propyl-1,3-propanediol, and mixtures thereof.

Adsorbents

The at least one feedstream and/or any agent described herein for treating the feedstream may also be contacted with at least one adsorbent. Adsorbers are used in order to remove impurities. In an embodiment, this may be advantageous, for example, when metal catalysts are used in one of the process steps. Often, cobalt, nitrogen, or sulfur compounds are removed by upstream and downstream adsorbers. Examples of adsorbers are alumina, molecular sieves, zeolites, activated carbon, clay earths optionally, impregnated with metals, silicagels, resins (e.g., acid resins), and mixtures thereof. Exemplary materials and methods for making and using adsorbers may be found, for example, in EP 1 002 852 B and U.S. Patent Application Publication No. 2005/0137442.

Other specific examples include without limitation molecular sieve 3A (activated 16 h @ 200° C. & vac), molecular sieve 13× (activated 1 h @ 200° C. & vac), Cameron SG6 carbon (12*40 mesh, coconut shell based BCT 4443), Cameron SG6 carbon (8*30 mesh, coconut shell based, BCT 4444), Norit GAC 830W 640316, BCT 4475 active coal, Keiselgel Fein silicagel (MN), Amberlyst 15 A, silica bound ex fr F103runE60, and Alcoa Selexsorb™ In an embodiment, processes and adsorbers as disclosed in, for example, PCT/EP2012/061365, filed Jun. 14, 2012, may be used.

Additionally, the at least one feedstream may undergo further processing, modification, and purification steps as described above (e.g., use of solvent extraction and/or adsorbents) or below and before or after the washing described above, prior to being introduced into the oligomerization reactor(s).

Hydration

In several classes of embodiments and prior to oligomerization, the feedstream may also be optionally hydrated (i.e., contacted with water) in addition to the washing described above. In an embodiment, sufficient water may be added to saturate the feedstream. The hydration process may use water with any pH, including acidic and alkaline water. In particular, the feedstream may comprise from about 0.01 to about 0.25, alternatively, from about 0.02 to about 0.20, and alternatively, from about 0.03 to about 0.10, mol % water based on the total hydrocarbon content of the feedstream. If desired and by way of example, the water content of the feedstream may be increased by passage through a thermostatted water saturator.

Selective Hydrogenation

The at least one feedstream may undergo a selective hydrogenation step. For example, further processing may include hydrogenation (e.g., using a supported palladium catalyst) to remove or reduce the concentrations of dienes and/or distillation to reduce the level saturated hydrocarbons. In other embodiments, polyunsaturated compounds, in particular 1,3-butadiene or the like, still present in small amounts may be further reduced by further selective hydrogenation steps (see, for example, EP 081041).

Drying

The at least one feedstream may also undergo a drying step. Any water present in the feed, which may stem, for example, from the washing may be removed by processes for drying. Suitable processes are, for example, the distillative removal of the water as an azeotrope.

Hydroisomerization

The process of hydroisomerization may be used to shift the positions of double bonds in the molecule. The classic example is the hydroisomerization of 1-butene to 2-butenes. At the same time, polyunsaturated compounds (for example residues of 1,3-butadiene) are hydrogenated to simple olefins. Hydroisomerization processes may be found, for example, in GB 2,057,006 and U.S. Patent Application Publication No. 2004/0097773.

Several other processes and steps are also contemplated. For example, in an embodiment of the invention, the at least one feedstream may be contacted with a heterogeneous catalyst under conditions suitable to hydrolyze nitrogen compounds to form a hydrolysis product as suggested in PCT/EP2012/061364, filed Jun. 14, 2012. In another embodiment of the invention, non-zeolite metal oxides disclosed in PCT/EP2012/061366, filed Jun. 14, 2012, may be used to remove nitrogen containing compounds from the feedstreams. In yet another embodiment of the invention, "guard beds" may be used as described in, for example, PCT/EP2012/061368 and PCT/EP2012/061369, both filed Jun. 14, 2012.

INDUSTRIAL APPLICABILITY

The oligomer product is useful in many applications and is the starting material for further hydroprocesses. For example, the oligomer product may be polymerized to produce polyolefins that have application in the plastic industry and synthetic basestocks for lubricants. The oligomer product may also be a blend component for fuels. The oligomer product may undergo hydroformylation and subsequently hydrogenation to produce alcohols. The alcohols may be used in industry such as, for example, solvents, or be incorporated into the production of detergents/surfactants. The alcohols may further be used in many other areas of industry such as, for example, undergoing esterification to produce esters that have application as plasticizers.

EXAMPLES

It is to be understood that while the invention has been described in conjunction with the specific embodiments thereof, the foregoing description is intended to illustrate and not limit the scope of the invention. Other aspects, advantages and modifications will be apparent to those skilled in the art to which the invention pertains.

Therefore, the following examples are put forth so as to provide those skilled in the art with a complete disclosure and description and are not intended to limit the scope of that which the inventors regard as their invention.

Single stage water wash experiments were completed to assess the impact of water pH on removal of 32 wt ppm N in the form of $NH_3$ (ammonia) from a $C_3$ rich olefin containing feedstream with the following composition: 49% propylene, 1% butene-1, 35% propane and 15% isobutane).

The experiments were conducted in the liquid phase under pressure and at ambient temperature. Starting water had an average pH 7.88 and N content of 2 mg/dm3 The water was treated to have an adjusted pH 10 by the addition of a NaOH solution. Further pH adjustments to provide additional water samples of pH 9, 8 and 7 were made by addition of monobasic sodium phosphate ($NaH_2PO_4$).

At each water pH, water was contacted with the $C_3$ rich olefin feedstream (49% propylene, 1% butene-1, 35% propane and 15% isobutane) containing 32 wt ppm N, in the form of $NH_3$. Water and the $C_3$ rich olefin containing feedstream containing $NH_3$ were contacted in a pressurized sample cylinder sample, shaken for 30 min, and allowed to rest for 60 min. The water and $C_3$ rich olefin containing feedstream were analyzed for N content and the final water pH was recorded. The $C_3$ rich olefin containing feedstream before and after contact with water were analyzed for nitrogen content using a Gas Chromatograph with a nitrogen Chemiluminsence detector (GC-NCD) (Agilent 255 Nitrogen Detector on 6890 GC with an Agilent HP 6890N (G 1530N) modified, using a CPSi18CB column) Nitrogen in water analysis was performed in accordance with UOP method 430. The results are as follows:

Example 1

A $C_3$ rich olefin containing feedstream (49% propylene, 1% butene-1, 35% propane and 15% isobutane) with 32 wppm N, in the form of $NH_3$ was contacted with water. The water having a pH 7 and $C_3$ rich olefin containing feedstream were contacted in a pressurized sample cylinder with a mass ratio of water to $C_3$ rich olefin containing feedstream of 0.13, shaken for 30 min, and allowed to rest for 60 min. The water and $C_3$ rich olefin containing feedstream were analyzed for N content and the final water pH was recorded.

Results are shown in Table 1.

TABLE 1

| $C_3$ Rich Stream N content before water contact (wt ppm N) | $C_3$ Rich Stream N content after water contact (wt ppm N) | Water N content before contact (wt ppm N) | Water N content after contact (wt ppm N) | Water pH before contact | Water pH after contact |
| --- | --- | --- | --- | --- | --- |
| 32 | 0.86 | 2 | 186 | 7 | 10.3 |

Example 2

A $C_3$ rich olefin containing stream (49% propylene, 1% butene-1, 35% propane and 15% isobutane) with 32 wppm N, in the form of $NH_3$ was contacted with water. The water having a pH 8 and $C_3$ rich olefin containing feedstream were contacted in a pressurized sample cylinder with a mass ratio of water to $C_3$ rich olefin containing feedstream of 0.13, shaken for 30 min, and allowed to rest for 60 min. The water and $C_3$ rich olefin containing feedstream were analyzed for N content and the final water pH was recorded. Results are shown in Table 2.

TABLE 2

| C₃ Rich Stream N content before water contact (wt ppm N) | C₃ Rich Stream N content after water contact (wt ppm N) | Water N content before contact (wt ppm N) | Water N content after contact (wt ppm N) | Water pH before contact | Water pH after contact |
|---|---|---|---|---|---|
| 32 | 0.76 | 2 | 194 | 8 | 10.2 |

Example 3

A $C_3$ rich olefin containing feedstream (49% propylene, 1% butene-1, 35% propane and 15% isobutane) with 32 wppm N, in the form of $NH_3$ was contacted with water. The water having a pH 9 and $C_3$ rich olefin containing feedstream were contacted in a pressurized sample cylinder with a mass ratio of water to $C_3$ rich olefin containing feedstream of 0.13, shaken for 30 min, and allowed to rest for 60 min. The water and $C_3$ rich olefin containing feedstream were analyzed for N content and the final water pH was recorded. Results are shown in Table 3.

TABLE 3

| C₃ Rich Stream N content before water contact (wt ppm N) | C₃ Rich Stream N content after water contact (wt ppm N) | Water N content before contact (wt ppm N) | Water N content after Contact (wt ppm N) | Water pH before contact | Water pH after contact |
|---|---|---|---|---|---|
| 32 | 0.73 | 2 | 176 | 9 | 10.2 |

Example 4

A $C_3$ rich olefin containing feedstream (49% propylene, 1% butene-1, 35% propane and 15% isobutane) with 32 wppm N, in the form of $NH_3$ was contacted with water. The water having a pH 10 and $C_3$ rich olefin containing feedstream were contacted in a pressurized sample cylinder with a mass ratio of water to dilute $C_3$ rich olefin containing stream of 0.13, shaken for 30 min, and allowed to rest for 60 min. The water and $C_3$ rich olefin containing feedstream were analyzed for N content and the final water pH was recorded. Results are shown in Table 4.

TABLE 4

| C₃ Rich Stream N content before water contact (wt ppm N) | C₃ Rich Stream N content after water contact (wt ppm N) | Water N content before contact (wt ppm N) | Water N content after Contact (wt ppm N) | Water pH before contact | Water pH after contact |
|---|---|---|---|---|---|
| 32 | 0.49 | 2 | 203 | 10 | 10.5 |

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the invention, additionally, they do not exclude impurities and variances normally associated with the elements and materials used. For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All priority documents are herein fully incorporated by reference for all jurisdictions in which such incorporation is permitted and to the extent such disclosure is consistent with the description of the present invention. Further, all documents and references cited herein, including testing procedures, publications, patents, journal articles, etc., are herein fully incorporated by reference for all jurisdictions in which such incorporation is permitted and to the extent such disclosure is consistent with the description of the present invention.

While the invention has been described with respect to a number of embodiments and examples, those skilled in the art, having benefit of this disclosure, will appreciate that other embodiments can be devised which do not depart from the scope and spirit of the invention as disclosed herein.

What is claimed is:

1. A process for the oligomerization of olefins, the process comprising providing at least one olefin feedstream that comprises 45 wt % or more combined propylene and propane based upon the total weight of the feedstream, and 5 ppm or more nitrogen from ammonia, contacting the at least one olefin feedstream with a liquid comprising alkaline water having a pH of from 7.5 to 10.5 to remove at least a portion of the ammonia to produce at least one treated olefin feedstream comprising 1 wt ppm or less nitrogen from ammonia and subsequently contacting the at least one treated olefin feedstream with a catalyst under oligomerization conditions to produce an oligomer product.

2. The process of claim 1, wherein the at least one olefin feedstream comprises propylene and propane and wherein the at least one olefin feedstream comprises 60 wt % or more combined propylene and propane, based upon the total weight of the feedstream.

3. The process of claim 1, wherein the alkaline water has a pH of 8.0 to 10.5.

4. The process of claim 1, wherein the liquid contacting of the at least one feedstream is in an amount of from 1 wt % to 100 wt %, based in the total weight of the feedstream.

5. The process of claim 1, wherein the process comprises a water to a hydrocarbon mass ratio of from 0.05 to 0.75, preferably 0.13.

6. The process of claim 1, wherein the process comprises a 20:1 or greater reduction of ammonia after contacting the at least one olefin feedstream with the liquid.

7. The process of claim 1, wherein the at least one olefin feedstream comprises 10 wt ppm or more of nitrogen present from ammonia.

8. The process of claim 1, wherein the at least one treated olefin feedstream comprises 0.2 wt ppm or less of nitrogen present from ammonia.

9. The process of claim 1, wherein the contacting occurs in a single stage or in an extraction unit.

10. The process of claim 1, wherein the liquid contacts the feed counter-currently in a column containing flow-distribution media such as tray or packing.

11. The process of claim 1, wherein the catalyst comprises mineral acids, zeolites, aluminum silicates, acid ion exchange resins, or mixtures thereof.

12. The process of claim 11, wherein the mineral acid is on a support material.

* * * * *